United States Patent
von Ahsen et al.

[11] Patent Number: 5,900,406
[45] Date of Patent: May 4, 1999

[54] USE OF ANTIBIOTICS OF THE TYPE 2-DEOXYSTREPTAMINE SUBSTITUTED WITH AMINOSUGARS TO INHIBIT GROWTH OF MICROORGANISMS CONTAINING GROUP I INTRONS

[75] Inventors: Uwe von Ahsen, Santa Cruz, Calif.; Julian E. Davies, Vancouver, Canada; Renée Schroeder, Vienna, Austria

[73] Assignee: NZYM, Inc., San Leandro, Calif.

[21] Appl. No.: 08/255,611

[22] Filed: Jun. 8, 1994

Related U.S. Application Data

[63] Continuation-in-part of application No. 07/910,436, Jul. 8, 1992, abandoned.

[30] Foreign Application Priority Data

Jul. 9, 1991 [AT] Austria ..................... 1375/91

[51] Int. Cl.[6] .................................. A61K 31/70
[52] U.S. Cl. ................ 514/35; 514/36; 514/37; 514/38; 514/39; 514/40; 514/41
[58] Field of Search ................. 514/35, 36, 37, 514/38, 39, 40, 41

[56] References Cited

U.S. PATENT DOCUMENTS

| 2,501,014 | 3/1950 | Wintersteiner et al. | 536/16 |
|---|---|---|---|
| 2,931,798 | 4/1960 | Umezana et al. | 536/13.7 |
| 3,976,768 | 8/1976 | Nara et al. | 536/16.1 |
| 4,029,883 | 6/1977 | Hiraga et al. | 536/13.7 |

*Primary Examiner*—Elli Peselev
*Attorney, Agent, or Firm*—Pennie & Edmonds LLP

[57] ABSTRACT

The invention described herein provides for methods of screening for compounds that can be used to prevent or inhibit the growth of microbial eukaryotes, particularly plant or animal pathogens. The screening methods of the invention involve the step of screening compounds for the ability to inhibit Group I intron I splicing. In addition, to directly screening for compounds that inhibit Group I intron splicing, the screening methods of the invention include screening for compounds that bind to prokaryotic 16S ribosomal RNA because of the correlation, described herein, between group I intron inhibition and binding to prokaryotic 16S ribosomal RNA. The range of possible compounds for screening by the screening methods of the invention is preferably limited to 2-deoxystreptamine derivatives.

Another aspect of the invention is to provide methods of treating or preventing infections with eukaryotic microbes by administering an effective amount of a compound that inhibits group I intron splicing. These compounds may be obtained by the screening methods of the invention.

14 Claims, 6 Drawing Sheets

THE GENTAMICIN GROUP

| | $R^1$ | $R^2$ | $R^3$ | $R^4$ | [CONC.]# |
|---|---|---|---|---|---|
| GENTAMICIN $C_{1a}$ | H | $NH_2$ | H | H | 1 μM |
| GENTAMICIN $C_2$ | Me | $NH_2$ | H | H | 1 μM |
| GENTAMICIN $C_1$ | Me | NHMe | H | H | 1 μM |
| GENTAMICIN B | H | $NH_2$ | OH | OH | 10 μM |
| G418 | Me | OH | OH | OH | 1 mM* |

THE KANAMYCIN GROUP

| | $R^1$ | $R^2$ | $R^3$ | $R^4$ | $R^5$ | [CONC.]# |
|---|---|---|---|---|---|---|
| TOBRAMYCIN | $NH_2$ | OH | H | $NH_2$ | H | 0.5 μM |
| KANAMYCIN A | $NH_2$ | OH | OH | OH | H | 5 mM* |
| KANAMYCIN B | $NH_2$ | OH | OH | $NH_2$ | H | 10 μM |
| KANAMYCIN C | OH | OH | OH | $NH_2$ | H | 5 mM* |

USE OF ANTIBIOTICS OF THE TYPE 2-DEOXYSTREPTAMINE SUBSTITUTED WITH AMINOSUGARS TO INHIBIT GROWTH OF MICROORGANISMS CONTAINING GROUP I INTRONS

RELATED APPLICATIONS

This application is a continuation-in-part of U.S. patent application Ser. No. 07/910,436, filed Jul. 8, 1992, now abandoned.

FIELD OF THE INVENTION

This invention is in the field of compounds and methods for inhibiting the splicing of group I introns, a type of intron found predominantly in lower eukaryotes.

BACKGROUND OF THE INVENTION

The discovery of catalytically active RNA has provided the basis for the evolutionary concept of an RNA world. It has been proposed that during evolution the functions of ancient catalytic RNA were modulated by low molecular weight effectors, related to antibiotics, present in the primordial soup. Antibiotics and RNA may have co-evolved in the formation of the modern ribosome (Davies, *J. Molec. Microbio.* 4, 1227–1232 (1990)). The experiments described herein demonstrate that a set of aminoglycoside antibiotics, which are known to interact with the decoding region of the 16S ribosomal RNA of *Escherichia coli.* (Moazed, D. & Noller, H. F. *Nature* 327, 389–394 (1987); Noller, H. F. *A. Rev. Biochem.* 53, 119–162 (1984); Cundliffe, E. in *The Ribosome* (eds Hill, W. E. et al.) 479–490 (Am. Soc. Microbiol., Washington 1990), inhibit the second step of splicing of the T4 phage-derived td intron. Thus catalytic RNA seems to interact not only with a mononucleotide (Bass, B. & Cech, T. R. *Biochemistry* 25, 44773–4477 (1986)) and an amino acid (Yarus, M. *Science* 240, 1751–1758 (1988)), but also with another class of biomolecules, the sugars. Splicing of other group I introns but not group II introns was inhibited. The similarity in affinity and specificity of these antibiotics for group I introns and rRNAs may result from recognition of evolutionarily conserved structures.

The first step of splicing, which is initiated by binding of exogenous guanosine to the G-binding site, is dependent on guanosine concentration. Once bound to the ribozyme, the 5' splice-site is cleaved and the nucleoside becomes covalently linked to the first nucleotide of the intron. The second step of splicing is initiated by nucleophilic attack of the 3' splice site by the free 3' hydroxyl group of the upstream exon. The splice site is cleaved and the exons are ligated (FIG. 1). (Cech, T. R. *A. Rev. Biochem.* 59, 543–568 (1990).) The genetic information carried by DNA is transcribed to RNA to mediate the process of gene expression. The coding region of RNA is very often interrupted by so called intervening sequences (introns). These introns must be removed from the coding regions (exons) to result in an uninterrupted sequence or functional RNA; the exons become spliced together. Depending on the splice mechanism, characteristic secondary structure, and cofactor dependence, several intron classes can be differentiated. The group I intron RNA can be folded in a characteristic set of stem and loop structure. These introns are removed by two consecutive transesterification reactions and an external guanosine or guanosine phosphate derivative is needed to initiate the splice reaction. This guanosine attacks, via its 3'-hydroxyl group, the 5'splice site and becomes covalently linked to the 5'end of the intron. The 3'-hydroxyl of the 5'exon now attacks the 3' splice site, the two exons become ligated and the intron is released. This reaction is autocatalytic, i.e., the reaction occurs in the absence of any protein enzymes or hydrolysis of energy rich bonds solely because of the ability of the intron RNA to fold in its active form. The reaction can be performed in vitro by synthesizing the RNA in vitro and incubating it in the presence of pH-buffer, magnesium ions and the cofactor guanosine (or GTP) (see Cech, Annual Review of Biochemistry, 1990, vol. 59, p. 543).

Group I introns have been found in messenger RNA (mRNA), ribosomal RNA (rRNA) and transfer RNA (tRNA) in microorganisms and organelles of all kingdoms (compare Michel & Westhof, Journal of Molecular Biology, 1990, vol. 216, p.585).

The group I intron provides an attractive target for antimicrobial agents because the intron is predominantly found in lower eukaryotes. The invention described herein provides methods for screening for compounds that inhibit group I intron splicing and methods for inhibiting microbial growth with these compounds.

Figure 1:
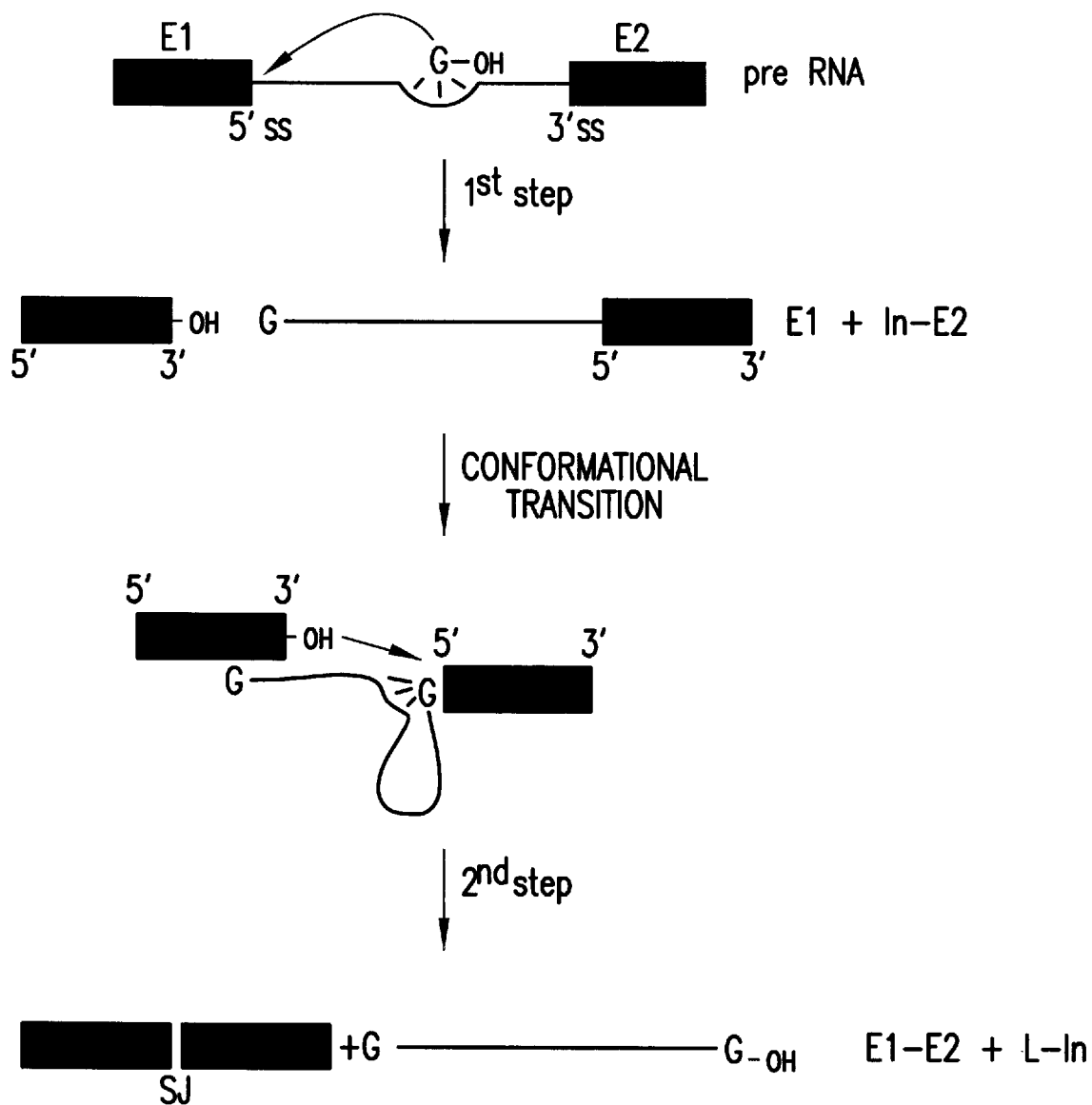
FIG. 1, Splicing pathway of group I introns. Solid bars indicate exons, lines indicate intron sequences; 5' ss, 3' ss and 5) indicate 5' and 3' splice sites and spliced junction, respectively. The first step of splicing is initiated by exogenous guanosine (G-OH) which attaches to the G-binding site, cleaves the 5' splice site by nucleophilic attack and becomes covalently added to the first nucleotide of the intron. For the second step of splicing the last nucleotide of the intron, always a G, has to enter the G-binding site (conformational change). The 3' OH group of the upstream exon attacks the 3' splice-site, which is cleaved and the exons ligated.

329–354, Addison-Wesley, London, (1983) "Conc" is the antibiotic concentration at which about 50% inhibition was observed. The "*" symbol indicates that no inhibition was found up to the indicated concentration.

SUMMARY

The invention described herein provides for methods of screening for compounds that can be used to prevent or inhibit the growth of microbial eukaryotes, particularly plant or animal pathogens. The screening methods of the invention involve the step of screening compounds for the ability to inhibit Group I intron I splicing. In addition, to directly screening for compounds that inhibit Group I intron splicing, the screening methods of the invention include screening for compounds that bind to prokaryotic 16S ribosomal RNA because of the correlation, described herein, between group I intron inhibition and binding to prokaryotic 16S ribosomal RNA. The range of possible compounds for screening by the screening methods of the invention is preferably limited to 2-deoxystreptamine derivatives.

Another aspect of the invention is to provide methods of reducing the growth rate of eukaryotic microbes, including treating or preventing infections, with by administering an effective amount of a compound that inhibits group I intron splicing. These compounds may be obtained by the screening methods of the invention. These compounds include gentamicin $C_{1a}$, gentamicin $C_2$, gentamicin $C_1$, gentamicin B, G418, tobramycin, kanamycin A, kanamycin B, kanamycin C, neamine, ribostamycin, neomycin B, paromomycin B, sisomicin, 5-epi-sisomicin, dihydrosisomicin, and 1-N-acetyl-sisomicin.

DESCRIPTION OF THE SPECIFIC EMBODIMENTS

The invention provides new methods of inhibiting the splicing of Group I introns. The application relates to the discovery that aminoglycoside compounds, especially compounds comprising a 2-deoxystreptamine moiety can inhibit the splicing of group I introns. While many 2-deoxystreptamine compounds substituted with aminosugars have been shown to have antibiotic properties against bacteria, the use of such compounds against group I intron containing microorganisms, primarily fungi, was not known prior to the invention described herein.

Thus, one aspect of the invention is to use compounds, particularly deoxystreptamine, substituted with aminosugars, to treat and/or prevent eukaryotic microbial, e.g., fungal, infections in humans, other animals, and plants, or to prevent the growth of microbial eukarotes in for purpose other than treating infections, such as to prevent food spoilage, deterioation of wood, and the like.

Another aspect of the invention is to provide methods of screening compounds for use in reducing the growth of microbial eukaryotes, including treating or preventing microbial pathogen infections, by screening for compounds that inhibit group I intron splicing. Methods for screening for compounds that inhibit group I intron splicing include (1) directly screening for compounds that inhibit splicing of group I introns in splicing assays and (2) screening for compounds that bind to prokaryotic ribosomal 16S RNA. One aspect of the invention described herein is the discovery that many compounds, especially 2-deoxystreptamines substituted with aminosugars, that bind to prokaryotic ribosomal 16S RNA are able to inhibit the splicing of group I introns. The subject invention makes these screening methods particularly advantageous because the field of compounds for screening in intron splicing inhibition assays or prokaryotic 16S ribosomal RNA binding assays may be limited to aminoglycosides, preferably 2-deoxystreptamines substituted with aminosugars, so as to substantially increase the probability of finding compounds that have the desired antimicrobial activity.

The assays for detection involve the step of adding a compound suspected of having the desired activity to an intron assay mixture. An intron assay mixture comprises a polynucleotide comprising a group I intron . The intron assay mixture further comprises any additional reagents required for the splicing the particular group I intron included in the assay mixture.

Another aspect of the invention is to provide compositions comprising inhibitors of group I intron splicing formulated as compositions so as to be adapted for certain types of administration, e.g., oral, parenteral, or topical. The group I intron inhibitor containing composition is preferably administered at the site of infection. Consequently, the preferred form of formulation for a given group I intron inhibitor is dependent on the location of the infectious organism in the host animal or the location in a host where a given infectious organism would be expected to initially invade. For example topical infections are preferably treated or prevented by formulations designed for topical application, whereas systemic infections are preferably treated or prevented by administration of compositions formulated for parenteral administration. Similarly, group I intron inhibitors may be suitably formulated for use in reducing the growth of microbial eukaryotes in a non-pharmacetuical context, e.g., so as act as a preservative.

The invention may be better understood by referring to the following examples. The following examples are offered for the purpose of illustrating the invention and should not be interperted as a limitation of the invention.

EXAMPLES

To monitor the splice process in vitro precursor RNA containing exon1, intron and exon2 was synthesized by in vitro transcription using bacteriophage RNA polymerase. During transcription, a radioactive labeled nucleotide was present in the nucleotide mixture and was incorporated in the RNA. This radioactive labeled RNA was then subjected to splicing conditions and after reaction the RNA splice products were separated from each other by electrophoresis on a denaturing acrylamide gel. The gel was dried and exposed for autoradiography.

Figure 2A:
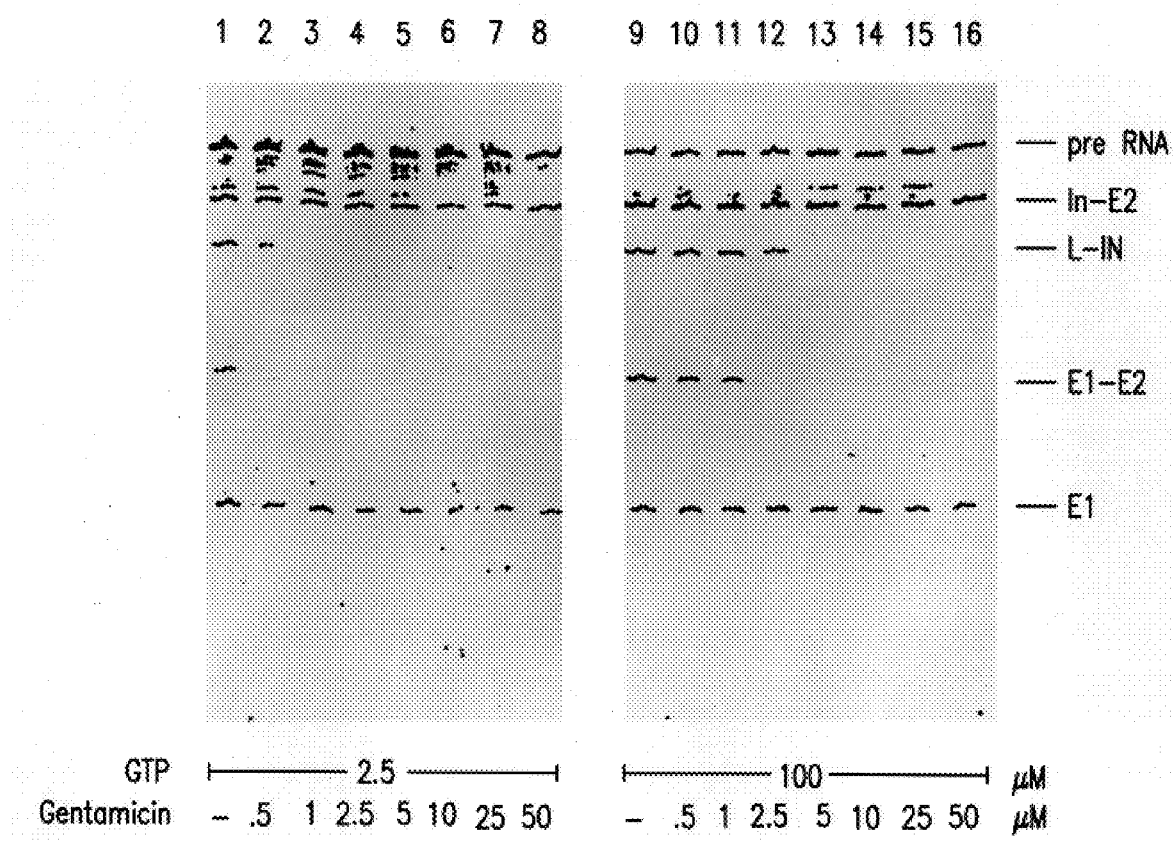
FIG. 2a, Splicing inhibition of the td intron by gentamicin. In vitro-transcribed and gel-purified[8] preRNA from a truncated version of the td intron[21] was incubated in a splicing buffer (50 mM Tris-HCl, pH 7.5, 5 mM MgCl2, 0.4 mM spermidine) for 10 min at 37° C. with GTP and gentamicin as indicated. Samples were separated on 5% acrylamide/7 M urea gels. RNA species are as follows: In-E2, intron-exon 2; L-ln, linear intron; E1–E2, ligated exons; E1, exon 1. Exon 2 does not accumulate.
Figure 2B:
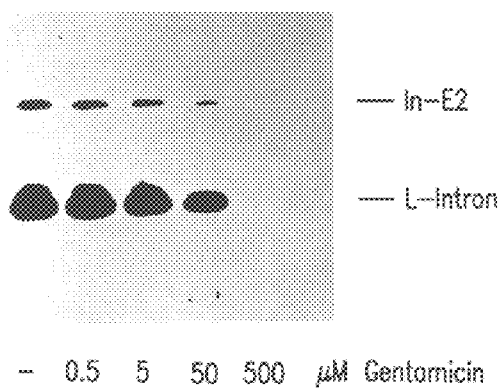
FIG. 2b, Splicing inhibition of the sunY intron by gentamicin. In a GTP incorporation assay[11] preRNA of the sunY construct SYC1.3[22] was incubated in splicing buffer (50 mM Tris-HCl, pH 7.5, 50 mM $NH_4Cl$, 3 mM $MgCl_2$, 0.4 mM spermidine) in the presence of 0.5 μCi [$^{32}$P]GTP (400 Ci mmol$^{-1}$) and increasing amounts of gentamicin. During the first step of splicing, guanosine becomes covalently added to the first nucleotide of the intron, resulting in labeled intron-exon 2 and linear-intron products.
Figure 2C:
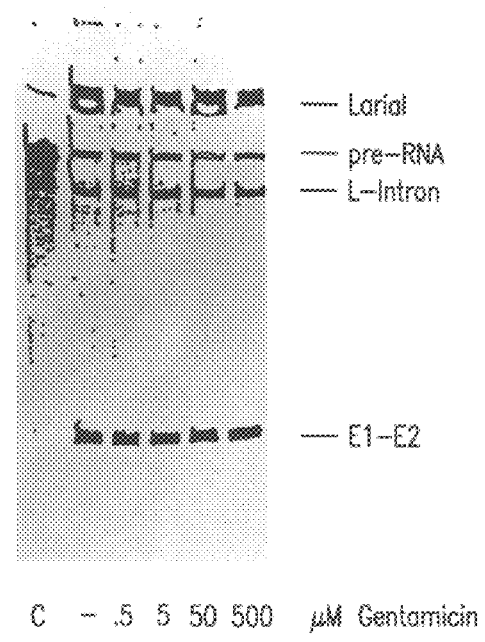
FIG. 2c, Precursor -A of the group II bli intron (first intron of the yeast mitochondrial apocytochrome b gene) was incubated in a splicing buffer (40 mM Tris-HCl, pH 7.5, 60 mM $MgCl_2$, 625 mM $(NH_4)_2SO_4$, 2 mM spermidine) at 42° C. for 60 min with increasing amounts of gentamicin as indicated. Splicing products were separated as in FIG. 2 A. C is an unincubated control.

As can be seen in the FIGS. 2a–2c which show autoradiographies of dried acrylamide gels, the splicing reaction of group I introns takes place only when external guanosine is added to the reaction.

The effect of aminoglycoside antibiotics, e.g., 2-deoxystreptamines substituted with aminosugars, on this splicing reaction was tested. The T4-phage derived td gene with a group I intron was selected as the Group I intron for testing (von Ahsen et al., Nature 353:368–370 (1991)). In FIG. 2a of the effect of gentamicin, a 4,6 disubstituted 2-deoxystreptamine, on the splicing process can be seen. Independent of the guanosine concentration the antibiotic inhibits the second step of splicing, i.e. exon ligation and release of the intron. The intermediate of the first step of splicing, intron-exon2 was unaffected.

FIG. 2b, shows the results of a similar experiment with a different group I intron, the sunY intron from T4-phage. Instead of internally labelling the RNA, a $32_p$ labelled GTP was added to sunY precursor RNA. The GTP became covalently linked to the 5'end of the intron and the intermediate intron-exon2 during the splice process. Again the splice reaction was inhibited by gentamicin, in this case even the first step of splicing.

To see whether this inhibition could be extended to all group I introns, the group I intron from the ribosomal RNA from *Tetrahymena thermophila* was tested for sensitivity towards gentamicin and again the splice reaction was inhibited. To test the specificity of this interaction of gentamicin with this type of catalytic RNA whether a different type of intron, a group II intron, is sensitive to gentamicin. The results from FIG. 2c show that this type of RNA is not affected in its catalytic activity by gentamicin.

Unspliced precursor RNA from the thymidylate synthase gene of the phage T4, which had been transcribed in vitro, and purified as previously described, (Schroeder, R., von Ahsen, U. & Belfort, M. *Biochemistry* 30, 3295–3303 (1991)) was incubated with increasing amounts of gentamicin under normal splicing conditions. FIG. 2a (lanes 1–8) shows the inhibition of splicing at a GTP concentration of 2.5 $\mu$M (the Michaelis constant ($K_m$) for GTP is 1 $\mu$M, Schroeder, R., von Ahsen, U. & Belfort, M. *Biochemistry* 30, 3295–3303 (1991)), whereas for lanes 9–16 the GTP concentration was 100 $\mu$M. At concentrations $\leq$2 mM, gentamicin has little effect on the first step of splicing whatever the guanosine concentration. By contrast, the second step, cleavage at the 3' splice-site and exon ligation, is completely inhibited at a concentration of 2.5 $\mu$M. The formation of ligated exons (E1–E2) and the appearance of a linear intron (L-In) are inhibited, whereas the intermediate products, intron-exon 2 (In-E2) and exon 1 (E1), remain nearly constant (FIG. 2a).

To analyze structure/activity relationships in the interaction of aminoglycosides with the ribozyme, we tested structurally related members of the families of aminoglycoside antibiotics (gentamicin, kanamycin and neomycin) in similar splicing inhibition assays (FIG. 2a). Tobramycin and neomycin B inhibited splicing at even lower concentrations than gentamicin, there being activity at a concentration as low as 0.5 $\mu$M which also affected the first step of splicing, albeit only at an antibiotic concentration of 100 $\mu$M.

Figure 3A:
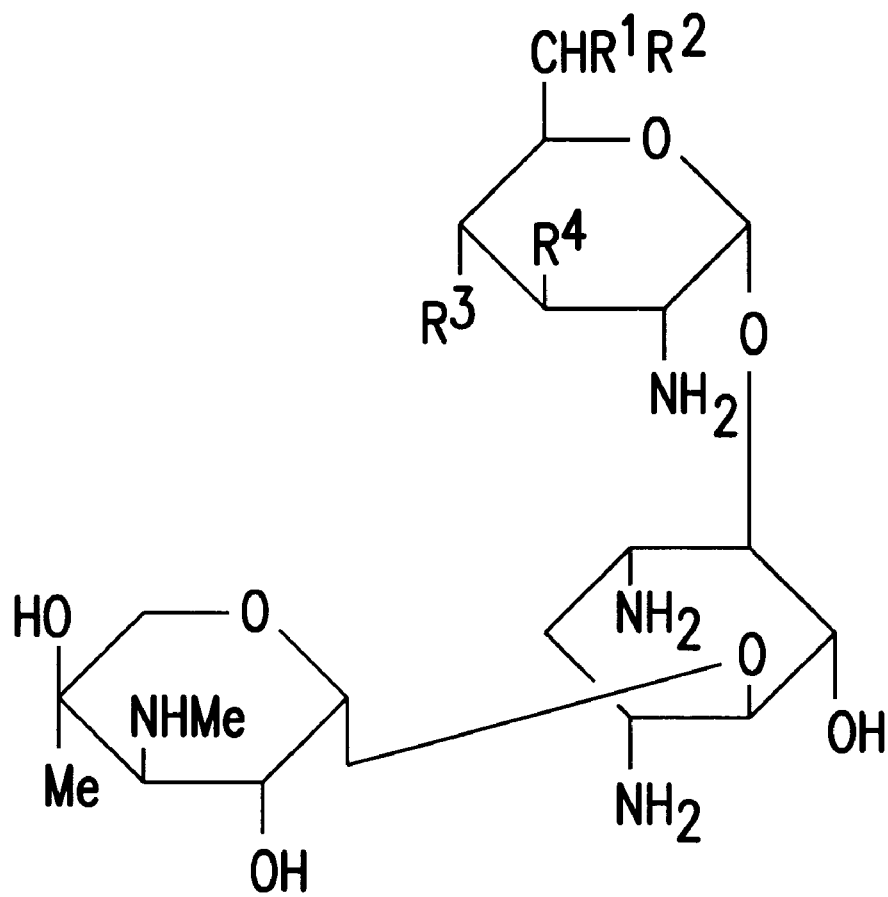
FIGS. 3a–c, Splicing experiments were done with the td intron as described in FIG. 2a, using several members of each family of aminoglycoside antibiotics (gentamicin, kanamycin and neomycin). Structures of the antibiotics can be found in Davies and Yagisaura in *Biochemistry and Genetic Function Of Commercially Important Antibiotics,* p.
Figure 3B:
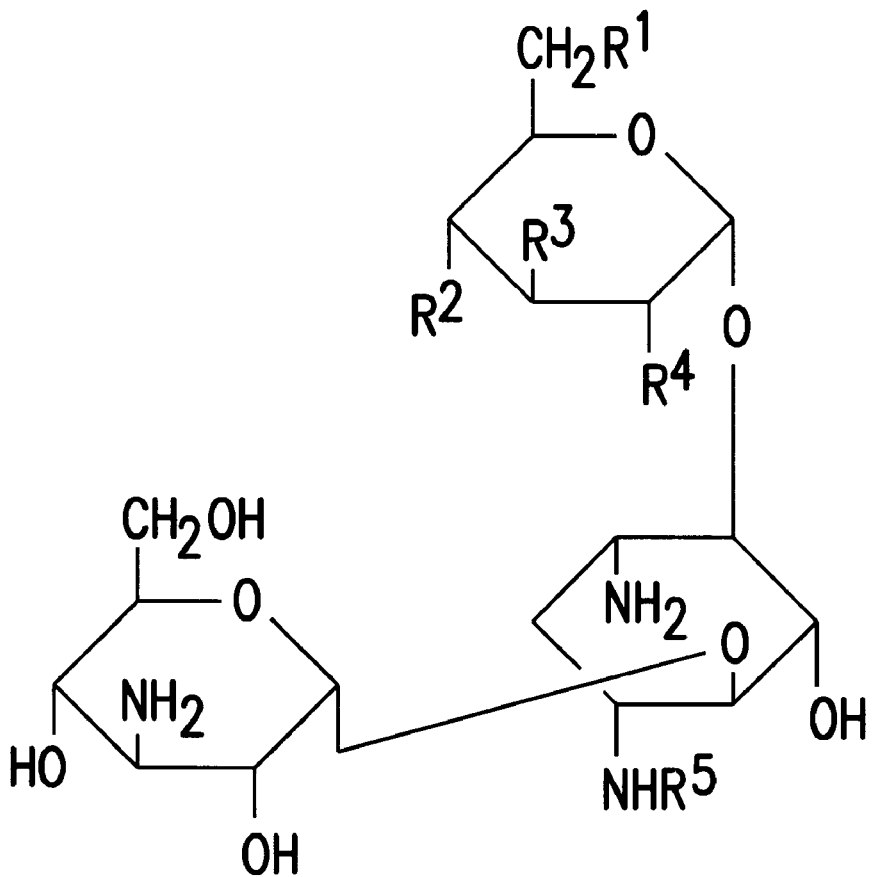
Figure 3C:
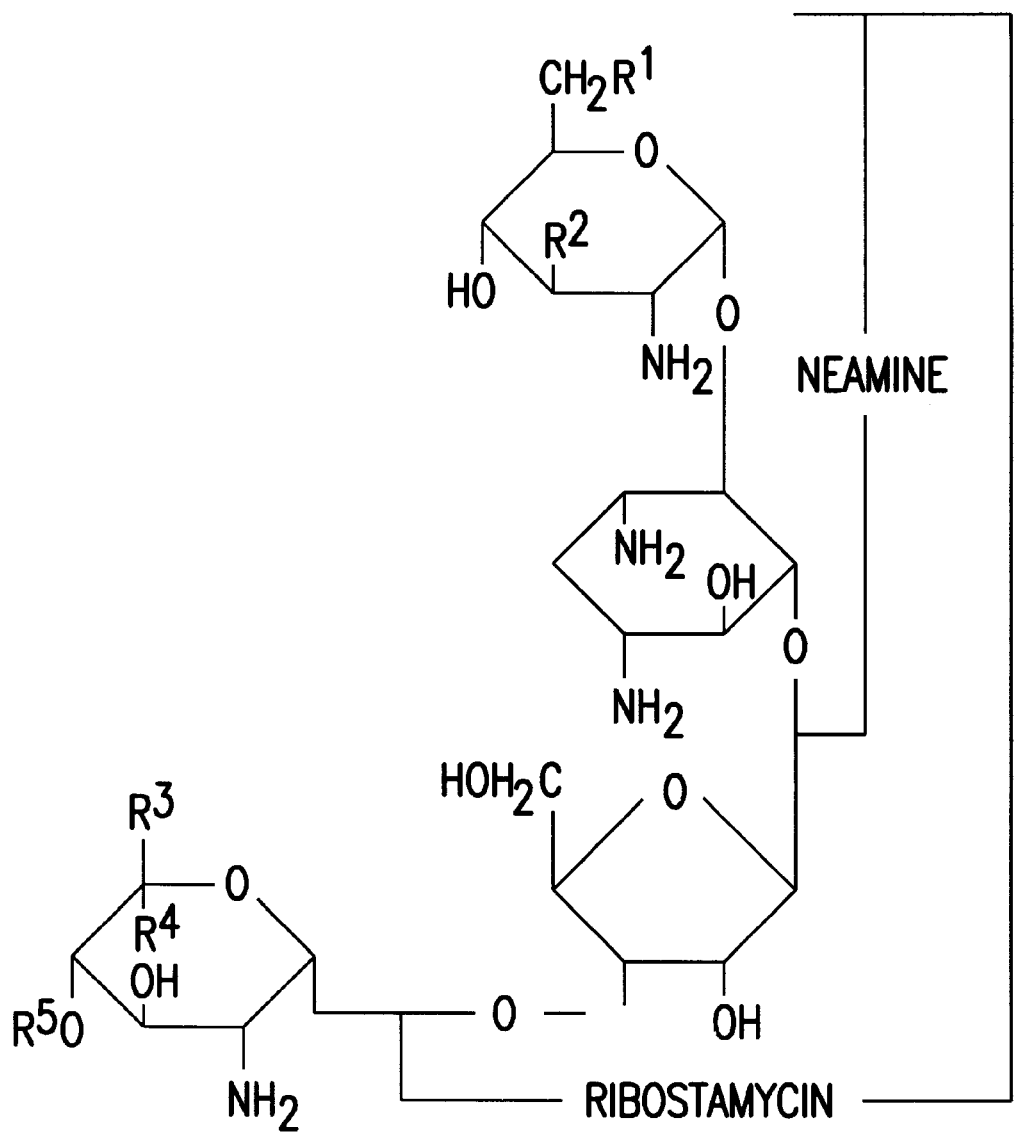

In FIGS. 3a–c is a list the antibiotics tested with their structures and the concentration at which about 50% inhibition was achieved. By comparing these results it becomes clear that the nature of the aminosugar is a factor in the inhibition of ribozyme function. To exclude nonspecific effects (for example, positive charge), different concentrations of spermidine were tested in combination with gentamicin, but spermidine had no influence on the inhibition caused by the antibiotic.

Other group I introns were tested for their sensitivity towards aminoglycosides. For the Tetrahymena rRNA, 50% inhibition of splicing occurs at ~100 $\mu$M gentamicin. A shortened version of the sun Y intron is sensitive to 10 AM neomycin Band 100 $\mu$M gentamicin. FIG. 2b illustrates the sensitivity of the sun Y intron towards gentamicin in a GTP-labelling experiment. (Ehrenman, K. et al. *Proc. Natl. Acad. Sci. U.S.A.* 53, 5875–5879 (1986)). The lower sensitivity of the sun Y and Tetrahymena introns towards both gentamicin and neomycin B could partially be explained by the stronger pairings of the P9.0 and P10 elements when compared with td (Michael, et al., *Nature* 342:391–395 (1989); Burke, et al., *Nature* 344:80–82 (1990); Michael, et al., *J. Molec. Biol.* 216:585–610 (1990)). As the first step of splicing in the td intron is also affected by the most potent antibiotic (neomycin B), the mechanism of inhibition for all aminoglycosides may be the same. As inhibition of splicing of the sun Y intron by gentamicin and neomycin B takes place independently of the guanosine concentration, we suggest that in contrast to the inhibition of splicing by streptomycin (Ahsen von, U. & Schroeder, R. *Nucleic Acids Res.* 19, 2261–2265 (1991); Ahsen von, U. & Schroeder, R. *Nature* 346, 801 (1990)), the antibiotic binds to a site distinct from the G-binding site (Michel, F., Hanna, M., Green, R., Bartel, D. P. & Szostak, J. W. *Nature* 342, 391–395 (1989)).

Inhibition in some cases (for example, tobramycin, neomycin B) occurred at concentrations equal to or lower than those required for inhibition of protein synthesis. Neomycin B is a potent inhibitor of protein synthesis and the most active aminoglycoside in inhibiting the splicing reaction (FIG. 3). Comparison of the structurally related tobramycin, kanamycin A, 8 and C shows the order tobramycin>kanamycin 8>kanamycin A>kanamycin C for splicing inhibition, and tobramycin equal to kanamycin 8>kanamycin A>kanamycin C for inhibition of in vitro translation (Benveniste, R. & Davies, J. *Antimicrob Agents Chemother,* 4, 402–409 (1973)). Positive charge does not seem to be a deciding factor and efficient inhibition of group I splicing is not a property of all antibiotics that inhibit translation: chloramphenicol, spectinomycin, hygromycin B, kasugamycin and crythromycin are inactive at millimolar concentrations. The aminoglycosides do not generally inhibit catalytic RNA functions as splicing of a group II intron (the first intron of the yeast mitochondrial apocytochrome b gene) was not inhibited by gentamicin or by tobramycin at concentrations $\leq$5 mM (FIG. 2c).

The protein synthesis inhibitors shown to be active in group I splicing reactions have a common characteristic, namely induction of translation errors. They interact with the ribosome through specific interactions with sequences near the 3' end of 16S rRNA (as identified by mutation or protection studies), disturbing the fidelity of codon-anticodon recognition. The aminoglycoside-sensitive group I intron and the region of 16S rRNA implicated in antibiotic binding sites show no sequence homology; it is probable that RNA conformation, not sequence, determines antibiotic binding sites.

Several features of the group I introns suggest similarities in structure with the translational machinery. The guanosine binding site of the group I introns is also an arginine-binding site and always an arginine codon (Bass, B. & Cech. T. R. *Biochemistry* 25, 4473–4477 (1986); Yarus, M. *Science* 240, 1751–1758 (1988); Michel, F., Hanna, M., Green, R., Bartel, D. P. & Szostak, J. W. *Nature* 342, 391–395 (1989); Yarus, M. & Christian, E. L. *Nature* 342, 349–350 (1990)). Furthermore, several proteins (Akins, R & Lambowitz, A. *Cell* 50, 331–345 (1987); Seraphin, B. Simon, M., Boulet, A. & Faye, G. *Nature* 337, 84–87 (1989)) that are components of the translational apparatus promote group I intron splicing.

Materials and Methods: In vitro splicing experiments were performed with a truncated version of the td gene, containing 79 nt of exon I, 265 nt of intron sequences containing only the catalytic core (delta P6-2) and 21 nt of exon H (Schroeder, von Ahsen, & Belfort, 199 1, Biochemistry 30, 3295). The plasmids containing the Tetrahymena rRNA intron and the yeast mitochondrial cob intron I (the group II intron) were pBGST7 (Been & Cech, 1986, Cell 47, 207) and pBSbII (Schmelzer and Schweyen, 1986, Cell 46, 557), respectively. The sunY intron is described in Michel et al. (1990, Genes & Development 4, 777). DNA was prepared by the alkaline-lysis procedure and linearized with appropriate restriction enzymes. Transcription was performed in a total volume of 20 μl at 30° C. for one (1) hour in buffer containing 40 mM Tris-HCl pH 7.5, 3 mM $MgCl_2$, 0.4 mM spermidine, 1 mM of each NTP, 5 mM DTIC, 10 units T7 RNA polymerase (Boehringer Mannheim), 10 μCi alpha-$^{35}$S-CTP and 10 units RNAse inhibitor (Boehringer Mannheim). The reaction mixture was loaded on a 5% polyacrylamide/7 M urea gel. Precursor RNA was cut out of the gel and soaked in 400 μl elution buffer (10 mM Tris-HCl pH 7.5, 10 mM EDTA, 3.5 M $NH_4OAc$, 0.1% SDS) for two hours. After ethanol precipitation, the RNA was dissolved in $H_2O$— before splicing experiments were performed the RNA was incubated in splicing buffer (40 mM Tris-HCl pH 7.5, 8 mM $MgCl_2$, 0.4 mM spermidine) for 2 min at 56° C. For splicing of the suny intron and the Tetrahymena intron 50 mM $NH_4Cl$ or 200 mM NaCl were added, respectively. Splicing was initiated by addition of guanosine at the appropriate concentration at 37° C. When splicing was to be inhibited by antibiotic, the antibiotic was added immediately before the guanosine. Splicing reactions were performed at 37° C. for 10'. The reactions were stopped by adding 45 μl of stop solution (2.5 mM EDTA, 0.1 mg/ml yeast tRNA), 25 μl 7.5 M $NH_4OAc$ and 150 μl 100% ethanol to a 5 μl reaction volume. After precipitation, samples were centrifuged for 10'at 12.000 rpm and the pellets were dissolved in 10 μl 80% for acrylamide containing 0.05% bromophenol blue and 0.05% xylene cyanole. Samples were separated on 5% acrylamide/7 M urea gels. After the electrophoresis the gels were dried and exposed for autoradiography.

Besides gentamicin, a variety of other 2-deoxystreptamine derivatives were tested for their efficiency to inhibit the splice reaction of group I introns. With some exceptions, they all show a strong capability to inhibit the reaction. Examples of active compounds are given in a table below and, together with the structure of the antibiotics, in FIGS. 3a–c.

TABLE 1

| Antibiotic | concentration* |
|---|---|
| Monosubstituted 2-Deoxystreptamines (Position) | |
| Neamine (4) | 200 μM |
| Apramycin (4) | 200 μM |
| Garamine (6) | 200 μM |
| 4,6-Disubstituted 2-Deoxystreptamines | |
| Gentamicin C | 1 μM |
| 2"-phospho-Gentamicin C | 100 μM |
| Gentamicin B | 10 μM |
| Sisomicin | 50 μM |
| 5-epi-Sisomicin | 0.5 μM |
| Dihydrosisomicin | 100 μM |
| 1-N-acetyl-Sisomicin | 100 μM |
| Tobramycin | 0.5 μM |
| Kanamycin B | 10 μM |
| 4,5-Disubstituted 2-Deoxystreptamines | |
| Neomycin B | 0.5 μM |
| Paromomycin | 100 μM |
| Lividomycin | 500 μM |

*Approximately 50% inhibition of the second splice step of the td intron

Besides their structure, these antibiotics have in common the target of the so-called decoding region of the 16S rRNA bacteria (Cundliffe, 1980. Antibiotics and prokaryotic ribosomes: action, interaction and resistance. In : Ribosomes. Structure, Function and Genetics. (Chambliss G. et al. eds.) University Park press Baltimore, p 555). Antibiotics known to interact with 23S rRNA were not able to inhibit the group I intron splice reaction, such as erythromycin, chloramphenicol, tiamulin, noursethricin, etc.

The specificity of the interaction of these 2-deoxystreptamine derivatives with group I introns opens the way to develop a new class of growth inhibitors of microorganisms that contain group I introns. This is to be distinguished from their effect on translation. It is particularly interesting because of the lack of group I introns in metazoa including all higher organisms and humans. In contrast, several fungi known to be human pathogens contain group I introns and our finding suggests the splicing of these introns as a target for chemotherapeutic agents. These fungi are normally not sensitive towards aminoglycoside antibiotics because they differ in the constitution of their ribosomes 2-deoxystreptamine derivatives could be used to specifically inhibit their growth without affecting the host. Another application could be in biotechnology: in fermenters growing microorganisms, the growth of unwanted, group I intron containing microorganisms could be prevented, etc. Alteratively, the catalytic function of RNA (ribozymes) could be regulated by the use of aminogycosides or their derivatives.

INCORPORATION BY REFERENCE

All patents, patents applications, and publications cited are incorporated herein by reference.

EQUIVALENTS

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

What is claimed is:

1. A method for inhibiting a eukaryotic microbial infection in a subject, comprising administering an effective amount of an aminoglycoside to the subject.

2. The method of claim 1 in which the eukaryotic microbe contains a group I intron.

3. The method of claim 1 in which the eukaryotic microbe is a fungus.

4. The method of claim 1 in which the hexose nucleus of the aminoglycoside is 2-deoxystreptamine.

5. The method of claim 4 in which the amino sugar substitutions are at positions 4 and 5.

6. The method of claim 4 in which the amino sugar substitutions are at positions 4 and 6.

7. The method of claim 1 in which the aminoglycoside is selected from the group consisting of gentamicin $C_{Ia}$, gentamicin $C_2$, gentamicin $C_1$, gentamicin B, G418, tobramycin, kanamycin A, kanamycin B, kanamycin C, neamine, ribostamycin, neomycin B, paromomycin B, sisomicin, 5-epi-sisomicin, dihydrosisomicin, and 1-N-acetyl-sisomicin.

8. A method for inhibiting growth of a eukaryotic microbe, comprising contacting the microbe with an aminoglycoside.

9. The method of claim 8 in which the eukaryotic microbe contains a group I intron.

10. The method of claim 8 in which the eukaryotic microbe is a fungus.

11. The method of claim 8 in which the hexose nucleus of the aminoglycoside is 2-deoxystreptamine.

12. The method of claim 11 in which the amino sugar substitutions are at positions 4 and 5.

13. The method of claim 11 in which the amino sugar substitutions are at positions 4 and 6.

14. The method of claim 8 in which the aminoglycoside is selected from the group consisting of gentamicin $C_{1a}$, gentamicin $C_2$, gentamicin $C_1$, gentamicin B, G418, tobramycin, kanamycin A, kanamycin B, kanamycin C, neamine, ribostamycin, neomycin B, paromomycin B, sisomicin, 5-epi-sisomicin, dihydrosisomicin, and 1-N-acetyl-sisomicin.

* * * * *